United States Patent [19]

Dragosits et al.

[11] Patent Number: 5,147,328
[45] Date of Patent: Sep. 15, 1992

[54] SYRINGE ASSEMBLY

[75] Inventors: Thomas J. Dragosits, Valley Cottage; Lennox Watts, Bronx, both of N.Y.; Steven Doumanis, Lincoln Park, N.J.

[73] Assignee: Becton, Dickinson and Company, Franklin Lakes, N.J.

[21] Appl. No.: 673,854

[22] Filed: Mar. 21, 1991

Related U.S. Application Data

[63] Continuation of Ser. No. 360,968, Jun. 2, 1989, abandoned.

[51] Int. Cl.$^5$ ............................................. A61M 5/00
[52] U.S. Cl. ................................. 604/218; 604/230; 222/386
[58] Field of Search ............... 604/187, 214, 218, 221, 604/230, 232; 222/386; 92/170.1

[56] References Cited

U.S. PATENT DOCUMENTS

| | | | |
|---|---|---|---|
| 2,514,575 | 7/1950 | Hein | 604/214 |
| 2,735,735 | 2/1956 | Abel | 604/230 |
| 2,902,034 | 5/1959 | Simmonds . | |
| 2,986,141 | 5/1961 | Hart | 92/170.1 |
| 3,346,147 | 10/1967 | Higgins et al. | 222/386 |
| 3,696,714 | 10/1972 | Panigati | 92/170.1 |
| 4,004,718 | 1/1977 | Wesley | 604/221 |
| 4,250,072 | 2/1981 | Flynn | 260/31.2 |
| 4,282,876 | 8/1981 | Flynn . | |
| 4,500,310 | 2/1985 | Christinger | 406/228 |
| 4,627,844 | 12/1986 | Schmitt | 604/264 |
| 4,724,508 | 2/1988 | Macy | 361/225 |
| 4,820,278 | 4/1989 | Balisky | 604/230 |

FOREIGN PATENT DOCUMENTS

| | | | |
|---|---|---|---|
| 103224 | 3/1984 | European Pat. Off. | 604/187 |
| 52889 | 4/1979 | Japan | 604/230 |
| 476501 | 9/1969 | Switzerland | 604/192 |

Primary Examiner—Stephen C. Pellegrino
Assistant Examiner—Ralph A. Lewis
Attorney, Agent, or Firm—John L. Voellmicke

[57] ABSTRACT

An operable syringe assembly comprises a barrel including a cylindrical coextruded body portion having a longitudinal axis. The body portion forms a side wall spaced from the axis defining a chamber for retaining fluid. The body portion includes an open proximal end and a distal end and further includes an inner portion of plastic material and a rigid portion of plastic material surrounding the inner portion. The rigid portion has a higher hardness than the inner portion. A plunger including an elongate shaft portion having a proximal end, a distal end and a rigid piston at the distal end is provided. The piston has an outside diameter greater than the inside diameter of the inner portion and a higher hardness than the inner portion. The piston portion is slidably positioned in fluid-tight engagement inside the barrel. The fluid-tight engagement is caused by the piston compressing the inner portion of the plastic material of the coextruded body portion. The proximal end of the plunger extends outwardly from the open proximal end of the barrel to facilitate moving the piston portion with respect to the barrel.

22 Claims, 4 Drawing Sheets

SYRINGE ASSEMBLY

This is a continuation of Ser. No. 360,968, filed Jun. 2, 1989, now abandoned.

BACKGROUND OF THE INVENTION

1. Field of the Invention

The present invention relates to syringes and more particularly concerns syringe assemblies with barrels having portions made of coextruded plastic materials.

2. Description of Related Information

Generally speaking, a hypodermic syringe consists of a cylindrical barrel, most commonly made of thermoplastic material or glass, having a distal end connected to a sharp needle cannula or adapted to be connected to a hypodermic needle assembly and a proximal open end adapted to receive a resilient stopper and plunger rod assembly. One of the purposes of the stopper is to provide a relatively air-tight seal between itself and the syringe barrel so that movement of the stopper up and down the barrel will cause liquid medication, blood or other fluids to be drawn into or forced out of the syringe through the distal end. The stopper is moved along the syringe barrel by applying axial force to the rigid plunger rod which is connected to the stopper and is sufficiently long as to be accessible outside of the barrel. The stopper should be sufficiently flexible so that it will seal the inside diameter of the barrel without requiring excessive force to move it up and down the barrel.

In order to assure an air-tight seal between the rigid syringe barrel and the resilient stopper, known prior art stoppers are manufactured with a larger outside diameter than the inside diameter of the syringe barrels they will be used in. The syringe-stopper combination is designed so that the stopper, when introduced into the syringe barrel, is compressed enough to provide adequate pressure between the syringe barrel and the stopper to seal this interface.

The resilient stopper, in prior art devices, should be chemically stable so that undesirable amounts of the various chemical components of the stopper do not enter the liquid contained in the syringe. Since hypodermic syringes are frequently used to inject medication into a human body or to withdraw blood for subsequent analysis it is not desirable to have stoppers introduce foreign substances which can affect the drug or the blood analysis. Hypodermic syringe stoppers are most commonly made of materials such as natural rubber or butyl rubber. Although the rubber stoppers have desirable physical properties they possess a number of disadvantages. For example, rubber stoppers contain additional chemical components such as fillers and vulcanizing accelerators which can exude to the surface and contact liquid in the syringe wherein blood test results or medication efficacy may be affected. Also, rubber stoppers are expensive to manufacture due to the long mold cycle time required by the vulcanizing step which takes place while the stoppers are in the mold.

Recognizing the above-mentioned deficiencies in rubber stoppers, it is desirable to provide a syringe assembly having a stopper or a piston made of plastic material. Normally, thermoplastic materials will be less expensive to manufacture due to shorter mold cycle times which result in improved productivity of the molding machinery. The possible effects of fillers and vulcanizing agents on the liquid contents of the syringe can be eliminated since these rubber additives are not necessary in the production of plastic stoppers or pistons. Also, the complexity of drug compatibility testing may be reduced when thermoplastic syringe stoppers are used in combination with a plastic barrel so that the stopper may be formed of materials having similar chemical properties to the barrel.

U.S. Pat. No. 4,500,310 to Christinger teaches an improved plunger rod design which allows the use of a resilient thermoplastic stopper. Christinger overcomes many of the cost and possible functional problems related to rubber stoppers but still requires an additional elastomeric stopper element to be connected to the plunger rod as in prior art syringes.

To fabricate a syringe using a rigid thermoplastic barrel and piston believed to be undesirable because the stresses produced by an interference fit substantial enough to provide an air-tight seal between the stopper and the barrel may result in a syringe assembly requiring an excessive amount of force to move the piston along the barrel to inject medication. Also, the tight fit between the barrel and the stopper, using thermoplastic materials, over a period of time may cause the piston and/or barrel to achieve a compression set. That is, the stresses of the interference fit between the stopper and the syringe can cause cold flow of the thermoplastic piston and/or barrel and thus the diameter of the stopper can become reduced, or the bore of the barrel enlarged so that the stopper may no longer effectively seal the contents of the syringe. Lubricants and expensive control of dimensional tolerances of the components can reduce some of these problems.

Although prior art syringes using rubber stoppers have served the medical community well over many years there are component cost and compatibility issues associated with rubber stoppers. Although the teachings of Christinger provide a substantial improvement by allowing the use of a thermoplastic resilient stopper there is still a need for a simple, straight-forward, reliable, easily fabricated syringe assembly having a plunger and piston made of low-cost rigid materials such as thermoplastics.

SUMMARY OF THE INVENTION

An operable syringe assembly of the present invention includes a barrel having a cylindrical coextruded body portion with a longitudinal axis, said body portion forming a side wall spaced from the axis defining the chamber for retaining fluid. The body portion includes an open proximal end and a distal end portion having a passageway therethrough in fluid communication with the chamber. The body portion includes an inner portion of plastic material and a rigid portion of plastic material surrounding the inner portion. The rigid portion has a higher hardness than the inner portion. A plunger including an elongate shaft portion having a proximal end, a distal end and a rigid piston portion at the distal end is provided. The piston portion has an outside diameter greater than the inside diameter of the inner portion and a hardness greater than the hardness of the inner portion. The piston portion is slidably positioned in fluid-tight engagement inside the barrel with the fluid-tight engagement being caused by the piston compressing the inner portion. The piston is capable of moving fluid from the chamber through the passageway upon its movement toward the distal end of the barrel and is capable of facilitating the drawing of fluid into the chamber through the passageway upon its movement away from the distal end of the barrel. The proximal end of the plunger extends outwardly from the proximal end of the barrel to facilitate moving the piston with respect to the barrel.

In another embodiment of the present invention an operable syringe assembly includes a barrel having a coextruded body portion with a longitudinal axis. The body portion forms a side wall spaced from the axis defining a chamber for retaining fluid. The body portion includes an open proximal end, a distal end, an inner portion of plastic material, and a rigid portion of rigid material surrounding the inner portion. The rigid portion has a higher hardness than the inner portion. A hub attached to the distal end, includes a passageway therethrough in fluid communication with the chamber. An elongate cannula having a proximal end, a distal end and a lumen therethrough is attached to the hub so that the lumen is in fluid communication with the passageway. Volume measuring indicia is provided on the side wall. A plunger including an elongate shaft portion having a proximal end, a distal end and a rigid piston portion at the distal end is provided. The piston portion has an outside diameter greater than the inside diameter of the inner portion and a higher hardness than the inner portion. The piston portion is slidably positioned in fluid-tight engagement inside the barrel. The fluid-tight engagement is caused by the piston compressing the inner portion wherein the piston is capable of moving fluid from the chamber through the passageway upon its movement toward the distal end. The piston is capable of facilitating the drawing of fluid into the chamber through the passageway upon its movement away from the distal end. The proximal end of the plunger extends outwardly from the proximal end of the barrel to facilitate movement of the piston portion with respect to the barrel.

In another aspect of the present invention a syringe barrel includes a cylindrical coextruded body portion having a longitudinal axis, said body portion forming a side wall spaced from the axis defining a chamber for retaining fluid, said body portion including an open proximal end, a distal end, an inner portion of plastic material, and a rigid portion of plastic material surrounding the inner portion. The rigid portion has a higher hardness than the inner portion. A hub member is attached to the distal end of the body portion. The hub member includes a passageway therethrough in fluid communication with the chamber.

DETAILED DESCRIPTION

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1-6, an operable syringe assembly 20 of the present invention comprises a barrel 21 including a, preferably transparent, coextruded body portion 22 having a longitudinal axis 23. The body portion forms a side wall 25 spaced from axis 23 defining a chamber 27 for retaining fluid. Coextruded body portion 22 includes an open proximal end 28 and a distal end 29. The body portion includes an inner portion of plastic material 31 and a rigid portion of plastic material 32 surrounding inner portion 31. Rigid portion 32 has a higher hardness and less resilient than inner portion 31.

For the purposes of the description of the present invention the term "distal end" is meant to refer to the end of the syringe assembly closest to the needle cannula or to the portion of the syringe assembly where a needle cannula may be attached, whereas the term "proximal end" is meant to refer to the end of the syringe assembly furthest from that portion of the syringe assembly having the needle cannula.

A hub portion 33 is attached to distal end 29 of the body portion. The hub includes a passageway (not shown) therethrough in fluid communication with chamber 27. An elongate cannula 34 having a proximal end 35, a distal end 37 and a lumen (not shown) therethrough. The cannula is attached to hub 33 so that the lumen is in fluid communication with the passageway.

Figure 1:
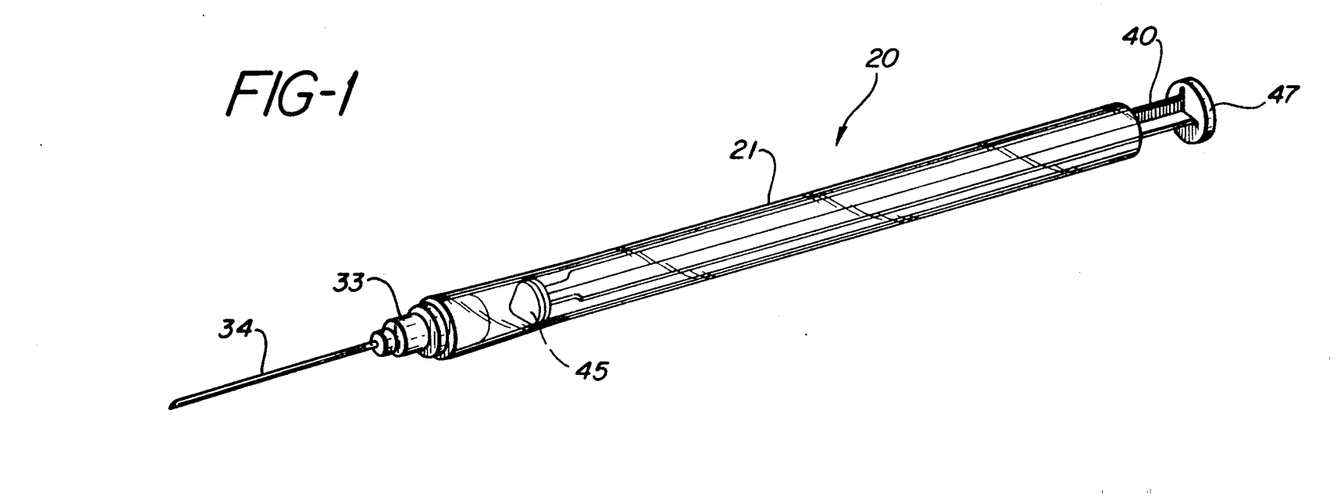
FIG. 1 is a perspective view of the syringe assembly of the present invention.
Figure 2:
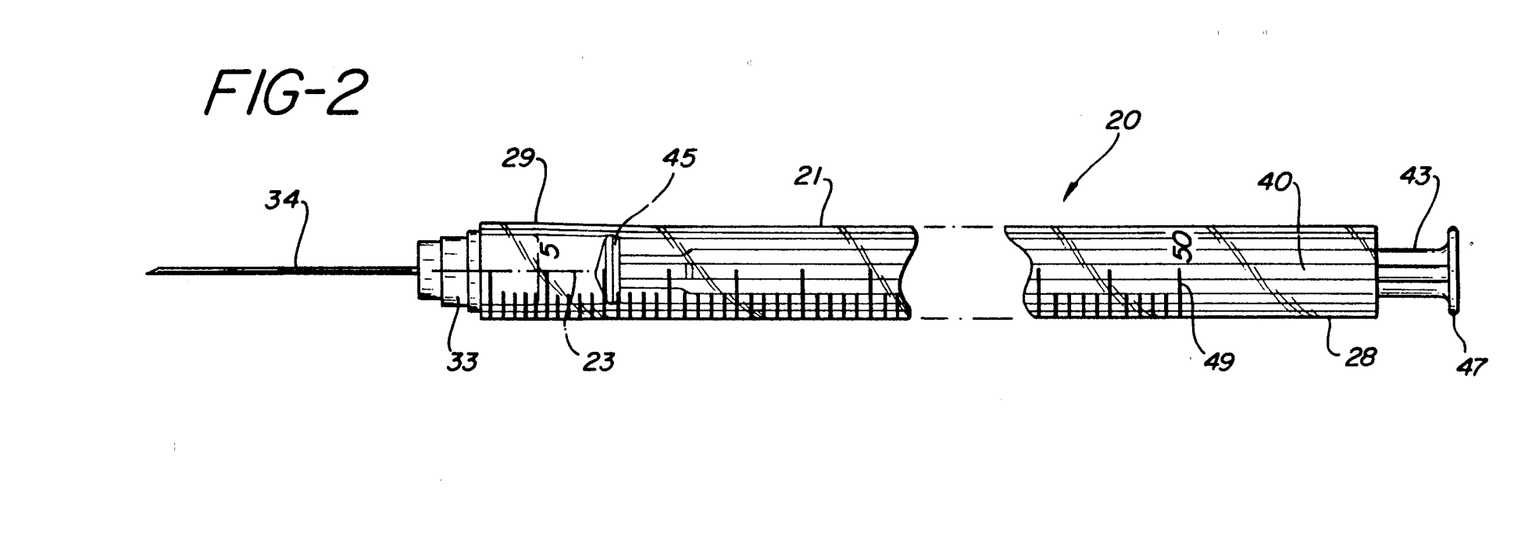
FIG. 2 is a side elevation view of the syringe assembly of FIG. 1.
Figure 3:
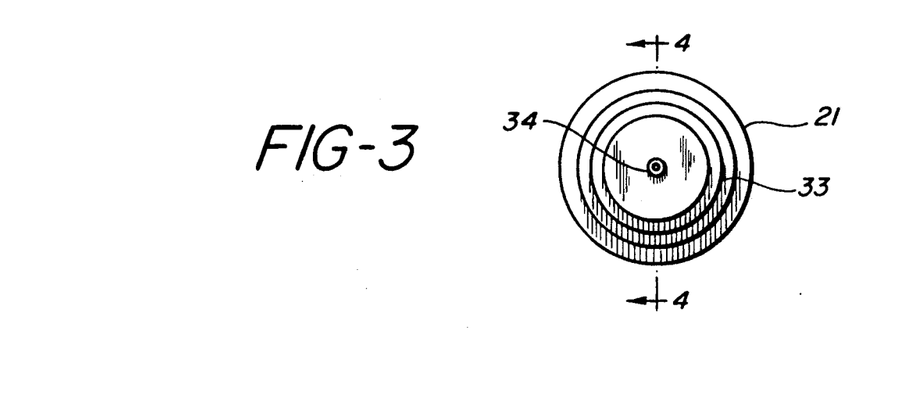
FIG. 3 is a side elevation view of the syringe barrel of FIG. 1 viewed from the distal end.
Figure 4:
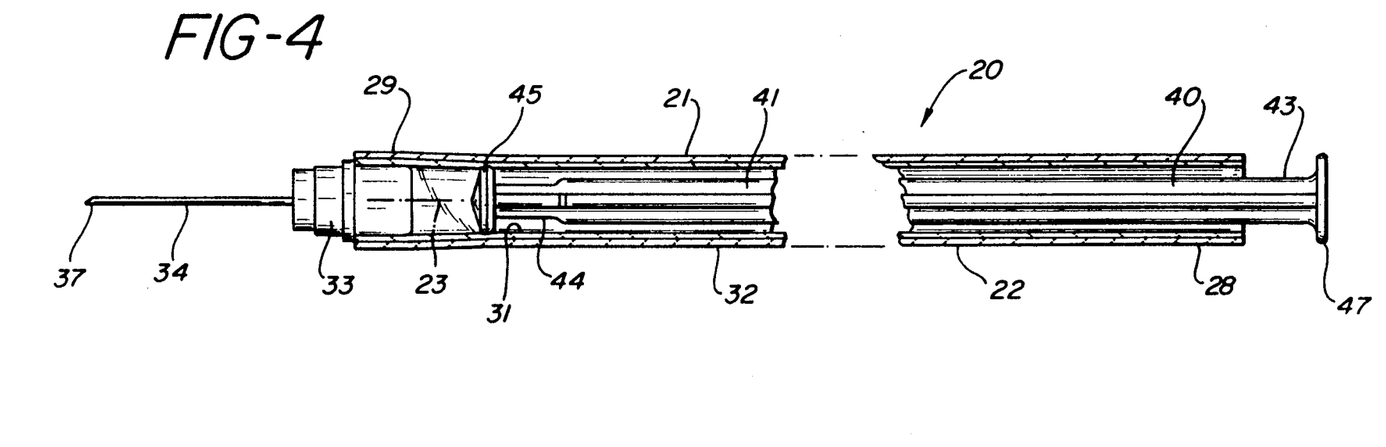
FIG. 4 is a cross-sectional view of the syringe assembly of FIG. 3 taken along line 4—4.
Figure 5:
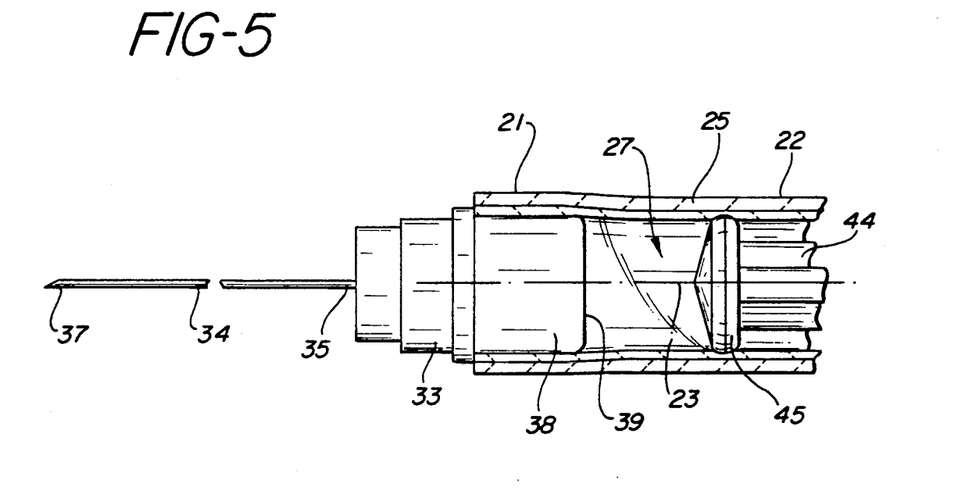
FIG. 5 is an enlarged partial view of the syringe assembly of FIG. 4 taken in the area of the piston.
Figure 6:
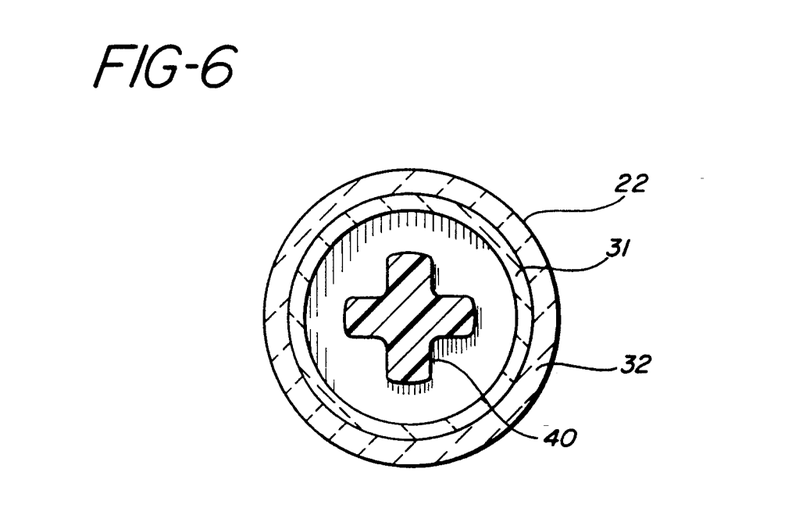
FIG. 6 is a cross-sectional view of the syringe assembly of FIG. 2 taken along line 6—6.

A plunger 40 includes an elongate shaft portion 41, a proximal end 43, a distal end 44 and a rigid piston portion 45 at distal end 44. Piston portion 45 has an outside diameter greater than the inside diameter of inner portion 31 of the coextruded body portion. The piston also has a higher hardness and is less resilient than inner portion 31. The piston portion is slidably positioned in fluid-tight engagement inside the coextruded body portion of the barrel. Fluid-tight engagement is caused by piston 45 compressing inner portion 31 of the coextruded body portion. This deflection is illustrated in FIGS. 4 and 5. The structure of the present invention wherein the piston is harder and less resilient than the inner portion of the barrel is a major difference between the instant invention and the prior art. Prior art disposable syringes rely on rubber or thermoplastic elastomer stoppers which are less hard and more resilient than the surrounding barrel to effectuate the fluid-tight seal between the stopper and the barrel. In the present instant invention this relationship is reversed, the harder less resilient member is the piston and most of the deflection occurs in the barrel rather than in the piston.

Rigid piston 45 is capable of moving fluid from chamber 27 through the passageway upon its movement toward distal end 29 of the body portion. Rigid piston 45 is also capable of facilitating the drawing of fluid into the chamber through the passageway upon its movement away from distal end 29 of the body portion. Proximal end 43 of plunger 40 extends outwardly from open proximal end 28 of the body portion to facilitate moving the piston with respect to the coextruded body portion of the barrel. Disc-shaped flange 47 is provided at proximal end 43 of the plunger. Disc-shaped flange 47 is a convenient structure for applying forces to the plunger with respect to the barrel.

In this embodiment, hub 33 is attached to the distal end of the coextruded body portion through an interference fit wherein the diameter of cylindrical proximal portion 38 of hub 33 is larger than the inside diameter of the distal end of the coextruded body portion. This form of engagement provides two advantages for the instant syringe assembly. First, the hub is attached to the body portion without the use of adhesives thus avoiding the extra cost of the adhesive and any possible problems with the adhesive being deposited within the chamber. Secondly, the interference fit between the hub and the body portion expands the inside diameter of the body portion immediately adjacent to back wall 39 of the hub so that during shipping the syringe may be assembled so that piston 45 rests against back wall 39. In this position slightly less stresses are created by the interaction of the piston deflecting inner portion 31 of the coextruded body portion. This lower stress region should minimize any possibility of creep or relaxation of the plastic components which may tend to reduce the effectiveness of the fluid-tight seal between the piston and the body portion.

In this preferred embodiment the piston has a diameter 0.196 inches (5.0 mm) and the coextruded body portion has an inside diameter of about 0.185 inches (4.7 mm). The thickness of the inner portion of plastic material is about 0.015 inches (0.38 mm) and the thickness of the rigid portion surrounding the inner portion is about 0.02 inches (0.51 mm).

It is within the purview of the present invention to include physically forming the coextruded body portion into a narrow opening containing the passageway without the use of a separate hub or, preferably, providing a separate hub as described hereinabove. It will be apparent to one skilled in the art that there are numerous ways to join a cylindrical body portion to a hub including the use of mechanical means, adhesive, ultrasonic welding, heat sealing or other suitable means and that the interference fit being used in the preferred embodiment is exemplary of these many possibilities.

It is also within the purview of the present invention to include a plunger wherein the piston portion is integrally formed with the elongate body portion forming a unitary structure as shown in the preferred embodiment of FIGS. 1-6. It is also within the purview of this invention to include a plunger with a separately formed piston portion which is attached to the elongate shaft portion using a variety of known techniques including mechanical joining, adhesive, ultrasonic welding, heat sealing or the like. This two-component construction may be desirable if a more expensive material is chosen for the piston portion such as polytetrafluoroethylene which exhibits a natural slipperiness or lubricity not found in other plastics.

In this preferred embodiment the inner portion of plastic material 31 of the coextruded body portion is formed of a resilient, preferably transparent, polyurethane having a hardness of 85 A on the Shore durometer scale. The hardness of 70 A to 90 A is desirable. It is within the purview of this invention to include virtually any hardness of material for the inner portion of plastic material so long as the effective hardness of the piston portion is greater than the hardness of the inner portion of the plastic material. Also in a syringe assembly the inner portion should be resilient enough and soft enough to effect a fluid-tight seal between the inner portion of the body portion and the piston.

In this preferred embodiment the piston portion is integrally formed with the elongate shaft portion to form a unitary plunger 40 formed of polysytrene. In this embodiment, the rigid portion of plastic material which surrounds the inner portion of plastic material in the coextruded body portion is formed of preferably transparent, rigid polyvinyl chloride. The preferred coextruded body portion contains two materials, the softer inner portion and the rigid outer portion which are fabricated into a cylindrical element using a coextrusion process. Such processes are described in U.S. Pat. Nos. 4,250,072 and 4,282,876 to Flynn and U.S. Pat. No. 4,627,844 to Schmidt.

Lubricants are used on prior art syringe stoppers and/or barrels to lower the forces required to move the rubber stopper along the barrel, especially after the prior art syringe assembly has been in storage a long time before use. In the instant invention careful choice of the materials used for the inner portion of the body portion and the piston may eliminate or reduce the amount of lubricant required for acceptable syringe assembly performance.

An important advantage and departure over the prior art of the present invention is the use of coextruded tubing to form part of the syringe barrel. The coextruded tubing can be manufactured more quickly and with a lower capital investment than injection molded barrel portions. The dual layers of the coextruded body portion allow the use of an inner portion which is softer and more resilient than the piston which eliminates the need for a separate rubber or thermoplastic elastomer stopper while the rigid portion which surrounds the inner portion provides the rigidity to this syringe structure to give the entire assembly a satisfactory structural integrity. It is within the purview of the instant invention to include more than two layers of material in the coextruded body portion such as the tri-layered tubing taught by Schmidt. The only requirement being that the rigid portion which surrounds the inner portion is of a higher effective hardness or rigidity.

The preferred embodiment of the syringe assembly of the present invention includes indicia on the barrel. This indicia may be volume measuring indicia 49 and/or instructions for use, or other trademark, or manufacturer information. Additional teachings in the prior art address improving the readability of volume measuring indicia by providing higher quality volume measuring indicia on the syringe barrel. In particular, a corona discharge treatment of the surface of various formed plastic articles such as syringe barrels will improve the compatibility of the surface with printing inks to provide higher quality printed indicia. Such a method is taught by Macy in U.S. Pat. No. 4,724,508.

Figure 7:
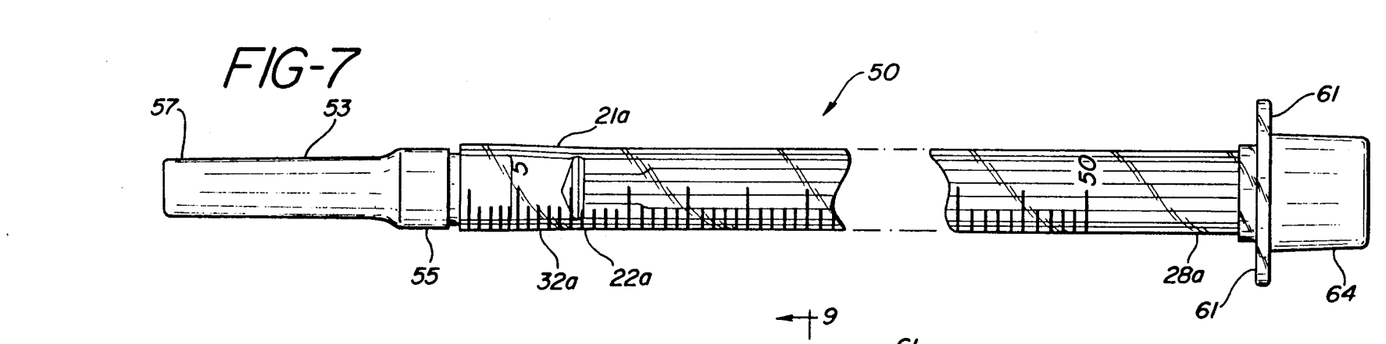
FIG. 7 is a side elevation view of the syringe assembly of the present invention including a proximal flange portion on the barrel, a needle shield and a plunger shield.
Figure 8:
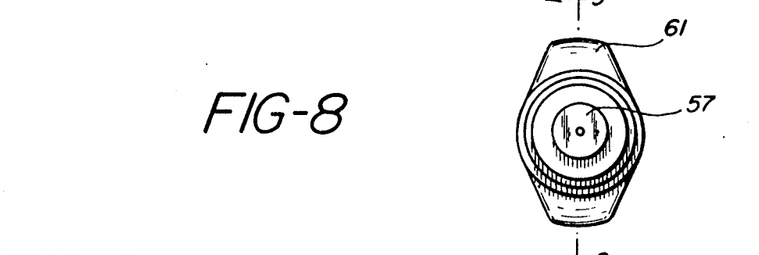
FIG. 8 is a side elevation view of the syringe assembly of FIG. 7 viewed from the distal end.
Figure 9:
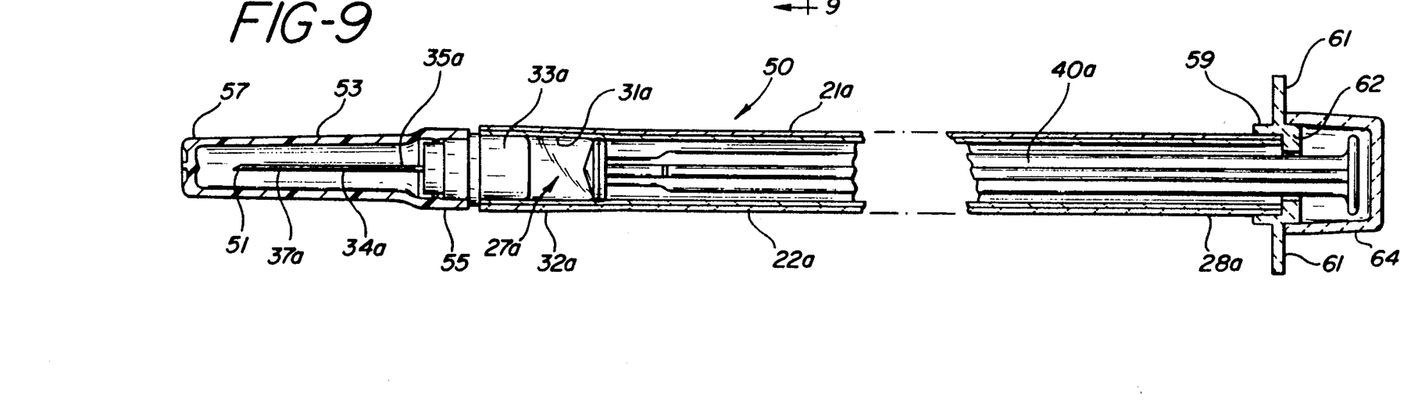
FIG. 9 is a cross-sectional view of the syringe assembly of FIG. 8 taken along line 9—9.

Referring now to FIGS. 7-9, an alternative embodiment of the syringe barrel of the instant invention is illustrated. In this alternative embodiment the structure of the syringe assembly is substantially similar to the syringe assembly of the embodiment of FIGS. 1-6. Accordingly, substantially similar components that perform substantially similar functions will be numbered identically to those components of the embodiment of FIGS. 1-6 except a suffix "a" will be used to identify those components in FIGS. 7-9. In this alternative embodiment, syringe assembly 50 includes a barrel 21a including a coextruded body portion 22a having an inner portion of plastic material 31a and a rigid portion of plastic material 32a surrounding the inner portion wherein the rigid portion has a higher hardness than the inner portion. A hub portion 33a is attached to the distal end of coextruded body portion 22a and includes a passageway therethrough in fluid communication with chamber 27a. An elongate cannula having proximal end 35a, a distal end 37a and a lumen therethrough is attached to the hub. Cannula 34a also includes a sharpened distal point 51. Cannula 34a is attached to hub 33a so that the lumen is in fluid communication with the passageway which is in turn in fluid communication with chamber 27a. The distal end of the cannula extends distally from the hub. A needle shield 53 having an open end 55 and a closed end 57. The needle shield removably engages hub 33a at the open end of the needle shield so that distal end 37a of cannula 34a is contained within the needle shield. The needle shield may be used to protect the sterility of the cannula before use and to prevent damage to the sharp distal point 51 of the cannula. In this embodiment the needle shield frictionally engages the hub through an interference fit wherein a portion of the needle shield has a smaller inside diameter than the corresponding portion of the hub to which it is removably engaged. Needle shields are well known in the art and may include many features such as apertures covered by breathable filters to aid in sterilization and various structures such as labyrinth passageways to allow sterilizing gases, when used, to pass freely into the syringe while resisting bacteria from following the same path. The needle shield shown herein is merely exemplary of the many possible structures for a needle shield and all these various structures are within the purview of the instant invention.

Open proximal end 28a of coextruded body portion 22a is connected to flange housing 59 and includes flange elements 61 which are provided to facilitate handling, positioning and operating the syringe assembly during filling and medication administration. Flange elements 61 also provide stability to the syringe by preventing it from rolling when it is placed on a table top or work surface. Flange housing 59 also includes housing boss 62 which has a circular outside diameter for frictionally and removably engaging plunger shield 64 which seals the open proximal end of the cylindrical body portion in much the same manner as the needle shield shields the needle end of the syringe. Again, numerous structures are available for a plunger shield, all of which fall within the purview of the instant invention. The structure will be determined in part on the functional requirements and the sterilization process utilized as well as whether additional protective packaging will be provided for the syringe assembly.

This alternative embodiment of FIGS. 7-9 can provide a self-contained syringe which acts as its own sterile package, when properly constructed and sterilized. The syringe is accordingly reduced to the smallest possible package. The self-contained package is believed to be preferred by various users such as diabetics who may carry syringes during the work day for providing insulin doses in accordance with their insulin regimen or supplemental doses as the need arises.

The syringe assembly of the instant invention and the syringe barrel of the instant invention when assembled into a syringe assembly may be used for injecting medication such as insulin utilizing well-known clinically safe techniques for drawing medication into the syringe and injecting medication into the patient.

The coextruded body portion of the syringe barrel of the present invention may be constructed of a wide variety of materials with polyurethane, polytetrafluoroethylene and thermoplastic elastomers being preferred for the inner portion of plastic material and polyvinyl chloride, polypropylene, polyethylene, polycarbonate and polystyrene being preferred for the rigid portion. Materials having a low compression set are preferred for the inner portion. Insulin compatible materials are preferable for the inner portion in embodiments of the instant invention being sold primarily to diabetic users. Although a wide variety of materials are suitable for use in the body portion of the syringe barrel of the instant invention the coextrusion process may limit the various combinations of inner portion and rigid portion materials to those which are compatible with each other within the coextrusion process. Transparent materials are preferred over opaque and translucent materials. It is also within the equivalency and the purview of the present invention to include dual layer barrels not produced by coextrusion but resulting in an equivalent body portion having an inner portion of plastic within a rigid portion wherein the rigid portion is harder than the inner portion.

A wide variety of rigid materials are suitable for the plunger and the piston, if the piston is separately fabricated, with injection molded polymers such as polystyrene, polyethylene, polypropylene, polytetrafluoroethylene, and polyvinyl chloride being desirable, and polystyrene being preferred. A lubricant, such as known medical grade silicone lubricants may be applied to the piston and/or the inner portion for reducing the force required to move the piston along the body portion.

Also, a wide variety of rigid materials is suitable for the needle shield, the flange housing and the plunger shield with injection moldable polymers such as polystyrene, polypropylene and polyethylene being preferred. The cannula is preferably made of medical grade stainless steel and attached to the hub through the use of various known means including mechanical connection, and adhesives such as heat curable and ultraviolet curable epoxy adhesives. A wide variety of commercially available inks may be used to form indicia on the barrel. The inks or coatings usable for the instant invention should be of medical grade quality. It is desirable that the syringe assembly of the present invention be sterile when used. Accordingly, all components used in the syringe assembly should be chosen to withstand the sterilization process being utilized.

Thus, it can be seen that the present invention provides a simple, straight-forward, reliable, easily fabricated, syringe assembly having a plunger and piston made of low cost rigid materials such as thermoplastics.

What is claimed is:

1. An operable syringe assembly comprising:
    a barrel including a cylindrical coextruded body portion having a longitudinal axis, said body portion forming a side wall spaced from said axis defining a chamber for retaining fluid, said body portion including an open proximal end and a distal end portion having a passageway therethrough in fluid communication with said chamber, said body portion having an inner portion of plastic material and a rigid portion of plastic material surrounding said inner portion wherein said inner portion and said rigid portion form an irremovably connected extrudate, said rigid portion having a higher hardness than said inner portion; and a plunger including an elongate shaft portion having a proximal end, a distal end and a rigid piston portion at said distal end having an outside diameter greater than the inside diameter of said inner portion, said piston having a higher hardness than said inner portion, said piston portion slidably positioned in fluid-tight engagement inside said barrel, said fluid-tight engagement being caused by said piston compressing said inner portion, said piston portion capable of moving fluid from said chamber through said passageway upon its movement toward said distal end, said piston portion capable of facilitating the drawing of fluid into said chamber through said passageway upon its movement away from said distal end, said proximal end of said plunger extending outwardly from said proximal end of said barrel to facilitate moving said piston portion with respect to said barrel.

2. The operable syringe assembly of claim 1 wherein said distal end portion is a separate hub member attached to the distal end of said body portion.

3. The operable syringe assembly of claim 2 wherein said hub includes a cylindrical proximal portion having an outside diameter greater than the inside diameter of said distal end of said cylindrical body portion, and said hub is attached to said distal end of said body portion through an interference fit between said circular proximal portion of said hub and the inside diameter of said cylindrical body portion.

4. The operable syringe assembly of claim 2 further including an elongate cannula having a proximal end, a distal end and a lumen therethrough, said cannula attached to said hub member so that said lumen is in fluid communication with said passageway and said distal end of said cannula extends distally from said hub.

5. The operable syringe assembly of claim 4 further including a needle shield having an open end and a closed end, said shield removably engaging said hub member at its open end so that said distal end of said cannula is contained within said needle shield.

6. The operable syringe assembly of claim 1 wherein said piston portion is integrally formed with said elongate shaft portion.

7. The operable syringe assembly of claim 1 wherein said body portion is transparent.

8. The operable syringe assembly of claim 1 wherein said rigid portion of said side wall is made of material selected from the group consisting of polyvinyl chloride, polypropylene, polyethylene, polycarbonate and polystyrene.

9. The operable syringe assembly of claim 1 wherein said inner portion of said side wall is made of material selected from the group of polyurethane, polytetrafluoroethylene, and thermoplastic elastomers.

10. The operable syringe assembly of claim 1 wherein said inner portion is made of polyurethane and said rigid portion is made of polyvinyl chloride.

11. The operable syringe assembly of claim 1 wherein said inner portion has a hardness of within the range of about 70 A to 90 A durometer.

12. The operable syringe assembly of claim 1 wherein said piston portion is made of material selected from the group consisting of polystyrene, polytetrafluoroethylene, polyethylene, polypropylene and polyvinyl chloride.

13. The operable syringe assembly of claim 1 wherein said side wall contains volume measuring indicia.

14. The operable syringe assembly of claim 1 wherein said side wall is subject to a corona discharge treatment and having volume measuring indicia applied to said corona discharge treated side wall.

15. A syringe barrel comprising:
a cylindrical coextruded body portion having a longitudinal axis, said body portion forming a side wall spaced from said axis defining a chamber for retaining fluid, said body portion including an open proximal end, and a distal end, said body portion having an inner portion of plastic material and a rigid portion of plastic material surrounding said inner portion wherein said inner portion and said rigid portion form an irremovably connected extrudate, said rigid portion having a higher hardness than said inner portion; and a hub member attached to said distal end having a passageway therethrough in fluid communicating with said chamber.

16. The syringe barrel of claim 15 wherein said inner portion is made of polyurethane and said rigid portion is made of polyvinyl chloride.

17. The syringe barrel of claim 15 wherein said inner portion has a hardness of within the range of about 70 A to 90 A durometer.

18. The syringe barrel of claim 15 wherein said body portion is transparent.

19. The syringe barrel of claim 15 further including an elongate cannula having a proximal end, a distal end and a lumen therethrough, said cannula attached to said hub member so that said lumen is in fluid communicating with said passageway and said distal end of said cannula extends distally from said hub.

20. An operable syringe assembly comprising:
a barrel including a coextruded body portion having a longitudinal axis, said body portion forming a side wall spaced from said axis defining a chamber for retaining fluid, said body portion including an open proximal end and a distal end, said body portion having an inner portion of plastic material and a rigid portion of plastic material surrounding said inner portion wherein said inner portion and said rigid portion form an irremovably connected extrudate, said rigid portion having a higher hardness than said inner portion;

a hub attached to said distal end having a passageway therethrough in fluid communication with said chamber, an elongate cannula having a proximal end, a distal end and a lumen therethrough, said cannula attached to said hub so that said lumen is in fluid communication with said passageway;

volume measuring indicia on said side wall; and a plunger including an elongate shaft portion having a proximal end, a distal end and a rigid piston portion at said distal end having an outside diameter greater than the inside diameter of said inner portion, said piston having a higher hardness than said inner portion, said piston portion slidably positioned in fluid-tight engagement inside said barrel, fluid-tight engagement being caused by said piston compressing said inner portion, said piston portion capable of moving fluid from said chamber through said passageway upon its movement toward said distal end, said piston portion capable of facilitating the drawing of fluid into said chamber through said passageway upon its movement away from said distal end, said proximal end of said plunger extending outwardly from said proximal end of said barrel to facilitate moving said piston portion with respect to said barrel.

21. The operable syringe assembly of claim 20 wherein said inner portion is made of polyurethane and said rigid portion is made of polyvinyl chloride.

22. The operable syringe assembly of claim 20 wherin said inner portion has a hardness of within the range of about 70 A to 90 A durometer.

* * * * *